United States Patent
Schembri et al.

(10) Patent No.: US 7,259,846 B2
(45) Date of Patent: Aug. 21, 2007

(54) LAB IN A CUVETTE

(75) Inventors: Carol T. Schembri, San Mateo, CA (US); Zhenghua Ji, Wilmington, DE (US); Hongfeng Yin, Cupertino, CA (US); William H. McAllister, Saratoga, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 23 days.

(21) Appl. No.: 11/214,498

(22) Filed: Aug. 30, 2005

(65) Prior Publication Data

US 2007/0081155 A1    Apr. 12, 2007

(51) Int. Cl.
*G01N 33/543* (2006.01)

(52) U.S. Cl. .................. 356/246; 356/244; 435/7.93

(58) Field of Classification Search ................ 356/246, 356/244

See application file for complete search history.

(56) References Cited

U.S. PATENT DOCUMENTS

| | | | |
|---|---|---|---|
| 3,097,928 A * | 7/1963 | Staunton | 422/100 |
| 4,286,881 A | 9/1981 | Janzen | |
| 4,420,254 A * | 12/1983 | Smeaton | 356/246 |
| 4,762,798 A * | 8/1988 | Deutsch | 436/67 |
| 5,674,699 A * | 10/1997 | Saunders et al. | 435/7.93 |
| 5,876,674 A * | 3/1999 | Dosoretz et al. | 422/91 |
| 6,459,080 B1 | 10/2002 | Yin et al. | |
| 6,628,382 B2 | 9/2003 | Robertson | |
| 6,943,883 B2 | 9/2005 | Fodgaard | |
| 7,022,286 B2 * | 4/2006 | Lemke et al. | 422/67 |
| 2007/0052956 A1* | 3/2007 | Blair | 356/246 |

* cited by examiner

*Primary Examiner*—Layla G. Lauchman
*Assistant Examiner*—Rebecca C. Slomski

(57) ABSTRACT

The present disclosure provides an apparatus for handling a liquid sample, wherein the apparatus includes integrated sample processing and sample evaluating components. The sample processing and evaluating components can include solid matrices that allow for optical measurement of a sample, or for the removal of contaminants from a sample. Methods for using the apparatus to handle liquid samples and evaluate sample components are also provided.

15 Claims, 2 Drawing Sheets

LAB IN A CUVETTE

BACKGROUND

In various research and testing fields it is necessary to accurately acquire fluid samples with volumes that may be as small as a few nanoliters. In these same fields, it is also often desirable to measure optical characteristics of the acquired fluid samples.

UV-Visible spectrophotometry provides a convenient analysis technique to determine the concentration, purity, and integrity of a biological sample. For instance, UV-Visible Spectrophotometry is commonly used to measure nucleic acid concentration. However, biological samples are often highly concentrated for downstream processing (such as microarray spotting or protein sample preparation for mass spectrometers). The absorbance of such samples can be above the saturation limit for typical spectrophotometers if the pathlength is about 10 mm. While the sample concentration range can be extended by diluting the sample, diluting a sample requires additional laboratory work and can result in errors. Other approaches are needed to extend the sample concentration range that can be evaluated by the instrument.

Sampling techniques used in conventional UV-Visible Spectrophotometers include utilizing a cuvette with an optical window and fixed optical pathlength that holds a sample in a semi-closed way, direct measurement of liquid sample in a sample container (e.g., a well) along with a real-time pathlength measurement, and using a cuvetteless sample held in semi-free space between optical fibers which define a light path from a light source to a detector.

The cuvette-based sampling technique is widely used in conventional UV-Visible spectrophotometers. Generally, a sample is pipetted into a cuvette that has either a 10 mm or 2 mm path length. This technique is limited for most biological samples since cuvettes typically used generally require a minimum of 1 mL sample, which is typically discarded after measurement. Large sample volume and loss is problematic for valuable biological samples which may be present in limited quantities. Further, transfer of relatively large sample quantities into a cuvette sometimes produces an air-bubble interface in the light path that can cause measurement error or void measurements. Additionally, a pathlength of 2 mm or 10 mm limits the sample concentration that may be measured to 1000 ng/ml for a DNA/RNA sample due to the limited dynamic range of absorbance of most spectrophotometers.

Cuvetteless sampling also suffers from drawbacks. For example, in cuvetteless sampling, typically a narrow beam of light is directed to a sample stage that consists of a 1-2 microliter liquid droplet suspended between two multi-mode optical fibers, one source-side fiber which provides light from a light source to the droplet and a detection-side fiber that guides light from the droplet to appropriate detection optics. The close proximity between the source-side and detection-side fibers allows enough of the light cone emanating from the source-side fiber to be collected by the detection-side fiber after passing through a liquid sample.

Cuvetteless instruments typically require a clamping surface that can be wetted with sample to avoid an air-bubble interface. Carry-over contamination from failure to completely remove previous samples is a source for error. Adding a small amount of sample (5 microliters) to the center of the clamping surface is also a complicated lab technique.

In summary, existing sampling techniques used in the conventional UV-Visible Spectrophotometers generally require too much sample, provide insufficient confidence in the sample application technique, may result in carry-over contamination, and may require pathlength determination and/or dilution of sample, over a range of solution concentrations. Additionally, the requirements of small sample collection, accurate path length determination, ease of handling and the ability to interface with other equipment pose conflicting demands on the design of any sampling apparatus.

There is, therefore, a need for a sampling apparatus that is capable of simultaneously meeting conflicting demands.

SUMMARY

The present invention relates to an apparatus for handling a liquid sample, wherein the apparatus includes integrated sample processing and sample evaluating components. The integrated sample processing may include a solid matrix for separation and/or addition of components to the liquid sample. The integrated sample evaluation component may include one or more windows sufficiently transparent for performance of an optical measurement.

DETAILED DESCRIPTION

Definitions

Figure 1:
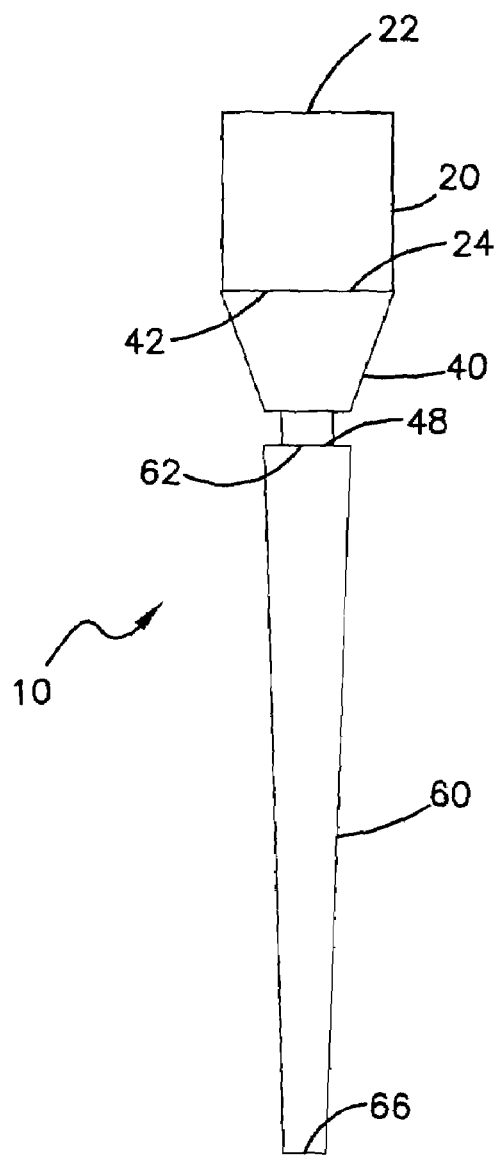
FIG. 1 is a schematic representation of an external view of an embodiment of an apparatus of the present invention.

Various embodiments of the present invention will be described in detail with reference to the drawings, wherein like reference numerals represent like parts throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

Unless defined otherwise below, all technical and scientific terms used herein have the same meaning as commonly understood by one of ordinary skill in the art to which this invention belongs. Still, certain terms are defined herein for the sake of clarity.

It must be noted that, as used in this specification and the appended claims, the singular forms "a", "an" and "the" include plural referents unless the context clearly dictates otherwise. Thus, for example, reference to "a biopolymer" includes more than one biopolymer, and the like.

It will also be appreciated that throughout the present application that words such as "upper" and "lower" are used in a relative sense only. Similarly, words "upstream" and "downstream" relate relative order of portions of the apparatus with reference to usual direction of liquid sample flow during use.

The term "assessing" and "evaluating" are used interchangeably to refer to any form of measurement, and includes determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent.

The term "optical" as used herein refers to properties related to the entire spectrum of electromagnetic radiation.

The term "using" has its conventional meaning, and, as such, means employing, e.g. putting into service, a method or composition to attain an end.

Apparatus

The present invention relates to an apparatus for handling a liquid sample, wherein the apparatus includes integrated sample processing and sample evaluating components. In an embodiment, an apparatus includes two or more bodies in fluid connection, wherein one body contains components for integrated sample processing and wherein another body contains sample evaluating components. In a further embodiment, the bodies are modular portions that operably connect. In an alternative embodiment, the bodies are included or constructed in a unified structure.

A liquid sample is loaded into an apparatus of the present invention for sample processing and evaluation. The liquid sample is loaded into the apparatus, and flows through one body wherein the liquid sample is processed. The processed liquid sample flows into another body wherein the processed liquid sample is evaluated, for example by UV/VIS spectroscopy. Liquid sample is collected, processed and evaluated within the apparatus. Benefits, such as, but not limited to elimination of transfers, reduction of contaimination, and increased speed and ease of use are recognized.

In an embodiment, the apparatus handles a liquid sample greater than 10 mL. In an embodiment, the apparatus handles a liquid sample volume equal to or less than 10 mL. In a further embodiment, the apparatus handles a liquid sample volume less than 5 mL. In a still further embodiment, the apparatus handles a liquid sample volume less than 1 mL. In yet another embodiment, the apparatus handles a liquid sample volume less than 500 microliters. In a yet further embodiment, the apparatus handles a liquid sample volume less than 100 microliters.

Integrated Sample Processing

In an embodiment, a liquid sample contacts or passes through a portion of the apparatus with integrated sample processing. In an embodiment, the apparatus includes a body having one or more components for integrated sample processing.

In an embodiment, a component for integrated sample processing separates material from a liquid sample. In an embodiment, a component for integrated sample processing includes a solid matrix. Solid matrices include, but are not limited to resin, membrane, frit or other solid matrix material to separate matter from a liquid sample. In an embodiment, the integrated sample processing collects particulate, whole cells and cell fragments thereby separating them from the liquid sample. In an embodiment, suitable solid matrix materials are porous so as to allow throughput of liquid sample. In a further embodiment, solid matrix materials have properties suitable for separation of sample constituents, including but not limited to size exclusion and adsorptive properties.

In another embodiment, the integrated sample processing adds a component to the liquid sample. In an embodiment, components that are added to the sample, include but are not limited to, affinity molecules and chemical reactants.

In an embodiment, other included components, in addition to or in alternative to a solid matrix, are chemical reactants or affinity molecules. Affinity molecules include, for example, but are not limited to, antibodies, receptors, and nucleic acids. Chemical reactants include, for example, but are not limited to, enzymes, labeling reagents, or cross-linking agents. In an embodiment, additional components are held in the apparatus by a solid matrix. In an alternative embodiment, additional components are held upon inner surfaces of one or more bodies of the apparatus.

Sample Evaluation

In an embodiment, a liquid sample fills or passes through a portion of the apparatus with an integrated sample evaluation component. In an embodiment, an integrated sample evaluation component includes one or more windows sufficiently transparent for performance of an optical measurement. In an embodiment, a body including an integrated sample evaluation component is designed to allow orientation with respect to a beam of electromagnetic radiation in order to enable alignment with respect to the beam in an optical instrument.

In an embodiment, the windows include a semi-transparent or a transparent material for performance of an optical measurement through the apparatus. In an embodiment, the integrated sample evaluation component includes a semi-transparent or a transparent material for performance of an optical measurement through the apparatus. In an embodiment, the body includes a semi-transparent or a transparent material for performance of an optical measurement through the apparatus.

Materials suitable for windows, integrated sample evaluation component, or body may vary and may include any at least partially transparent material, for example, a polymeric material such as polyimide, polycarbonate, polystyrene, polyolefin, fluoropolymer, polyester, a nonaromatic hydrocarbon, polyvinylidene chloride, polyhalocarbon, such as polycholortrifluoroethylene. Polyolefins may include polyethylenes, polymethylpentenes and polypropylenes, and fluoropolymers may include polyvinyl fluorides. Other materials glass, quartz, silica, silicon rubber, such as crosslinked dimethyldisiloxane, or materials used in optical crystals, such as sapphire or garnet (e.g., undoped Yttrium Aluminum Garnet).

In an embodiment, the material transmits light with a range of about 200-1100 nm. In an embodiment, the material transmits light in a range from about 300-800 nm. In an embodiment, the material transmits light in a range from about 200-400 nm. In an embodiment, the material transmits light of a wavelength greater than about 900 nm.

In an embodiment a body including at least one intregrated sample evaluation component is operatively connected to at least one other body of the apparatus. In an embodiment, there are a plurality of bodies including at least one integrated sample evaluation component. In one aspect, at least two of the plurality of bodies including integrated sample evaluation components comprise different optical properties. In an embodiment, one body transmits UV and/or visible light, while another body transmits fluorescent light.

In an embodiment, a sample evaluation component comprises windows sufficiently transparent to allow optical measurement in a range of about 200-1100 nm. In an embodiment, the sample evaluation component comprises windows sufficiently transparent to allow optical measurement in a range of about 300-800 nm. In an embodiment, the sample evaluation component comprises windows sufficiently transparent to allow optical measurement in a range of about 200-400 nm.

In an embodiment, at least one integrated sample evaluation component has a pathlength. Pathlength is dependent on the internal dimensions of the sample evaluation component at the position wherein a beam is oriented through the apparatus of spectroscopic measurement. In an embodiment, the body including a sample evalution component for spectroscopic measurement has a uniform pathlength. In an embodiment, the sample evaluation component has a pathlength of 10 mm or less. In an embodiment, the sample evaluation component has a pathlength of 5 mm or less. In an embodiment, the sample evaluation component has a pathlength of 2 mm or less. In an embodiment, the sample evaluation component has a pathlength of 1 mm or less. In an alternative embodiment, the determination of pathlength requires use of instruments such as level detectors or position sensors.

In an embodiment, materials and dimensions are selected to ensure that a measured signal relating to a sample within a body of the apparatus remains within the limit of the linear range for measurements by a particular detection device with which the apparatus of this invention is used. Suitable detection devices include, but are not limited to spectrophotometer, photometer, and spectrofluorometers.

Other

In an embodiment, the bodies of the apparatus are operatively connected. In an embodiment, the bodies are permanently operatively connected. In an alternative embodiment, two or more bodies are temporarily operatively connected. In an embodiment, one or more of bodies are adhesively bonded together with adhesive and including appropriate surface treatment if necessary. In an embodiment, one or more of bodies additionally include tabs or snap fits for tension fitting into an appropriately configured interface on an adjoining body. In an embodiment, the bodies are ultrasonically welded together, spin welded together, or solvent bonded. In an embodiment, the bodies are two-color injection molded. In an embodiment, the bodies are joined by other similar techniques.

In an embodiment, one or more of bodies are constructed as one unit. In an embodiment, one or more bodies are separately contracted. In an embodiment, one body, for example, a second body 40 described below, is insert injection molded into one or more adjacent bodies. In the embodiment of the apparatus, the material used for each body of the apparatus may be different in order to optimize separately the material used in each body with respect to the intended function of each body (for example, sample acquisition, optical measurement, pipette interface).

In an embodiment, the ends and internal passageway of each body is optimized separately. In an embodiment, a stop junction is introduced to affect a capillary break in an internal passageway. In a further embodiment, a stop junction is introduced to retain liquid sample in a sample evaluation component. In an embodiment, liquid sample is retained in a sample evaluation component by capillary action.

In an embodiment, an apparatus for handling a liquid sample additionally includes one or more additional integrated sample processing components. In a further embodiment, additional integrated sample processing occurs upstream from the sample evaluation component. In alternative further embodiment, additional integrated sample processing occurs downstream from the sample evaluation component. In a still further embodiment, the sample evaluation output data indicates and/or causes further sample processing.

In an embodiment, a quantity of liquid sample is collected in the evaluation component of the second body portion of the apparatus after flowing through the first body. In a further embodiment, a quantity of liquid sample is collected in a portion of the apparatus, in addition to the evaluation component or in alternative to the evaluation component. In an embodiment, a portion of the apparatus for collection of a quantity of liquid sample is in the first body. In an embodiment, a portion of the apparatus for collection of a quantity of liquid sample is in the second body. In an embodiment, a portion of the apparatus for collection of a quantity of liquid sample is in the third or other additional body. In an embodiment, an apparatus for handling a liquid sample additionally includes a sample collection portion and a passage or opening for adding, removing, or affecting the liquid sample.

In an embodiment, the apparatus, including one or more bodies thereof, includes additional portions, such as but not limited ports, connectors, openings or other means for further addition to, removal from, evaluation or processing of the liquid sample. In an embodiment, an apparatus for handling a liquid sample additionally includes a sample intake portion. In an embodiment, an apparatus for handling a liquid sample additionally includes a portion for operatively connecting to a device for aspirating liquid.

Illustrated Embodiments

In one embodiment, an apparatus for handling a liquid sample is structured similarity to a pipet tip. Liquid sample is brought up into the tip, through a sample processing component, and to a sample evaluation component, for ready evaluation, for example, by UN/VIS spectroscopy. One such embodiment is further described below.

Figure 2:
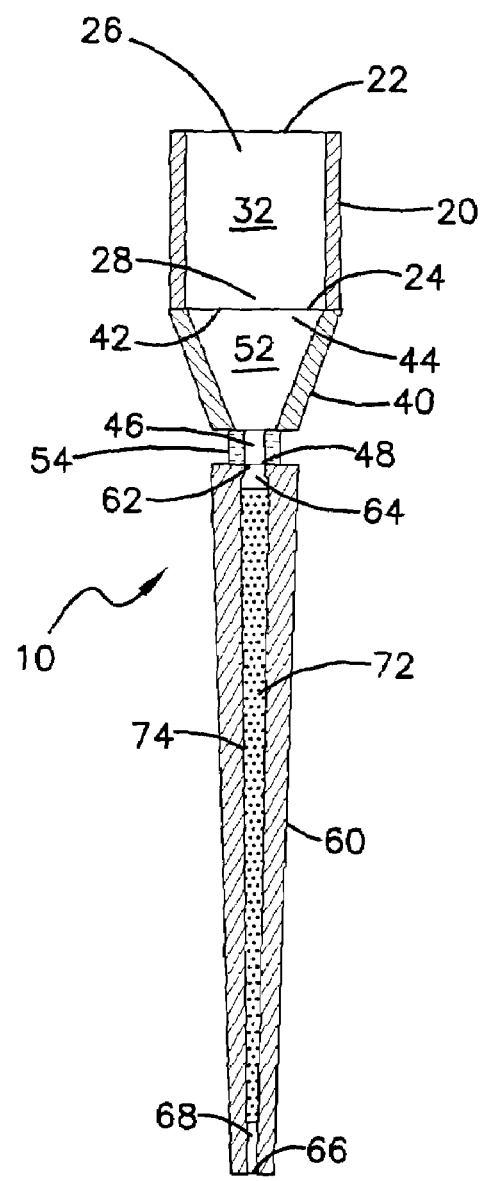
FIG. 2 is a cross-sectional view of the embodiment shown in FIG. 1.

One embodiment of an apparatus for handling a liquid sample is shown in FIGS. 1 and 2. The apparatus 10 includes three bodies, a first body 20, a second body 40, and a third body 60. Each body 20, 40, 60 has openings at opposite ends and defines an internal passageway. The first body 20 is an aspiration body and has a first opening 26 at the first end 22, a second opening 28 at a second end 24 and a passageway 32 connecting the first opening 26 to the second opening 28.

The second body 40 is a measurement body and has a first opening 44 at a first end 42, a second opening 46 at a second end 48, and a passageway 52 connecting the first opening 44 to the second opening 46.

The third body 60 is an intake body and has a first opening 64 at a first end 62, a second opening 68 and a second end 66, and a passageway 72 connecting the first opening 64 to the second opening 68. Passageway 72 contains solid matrix material 74. Solid matrix material 74 is porous so as to allow passage of liquid sample through passageway 72.

The first end 42 of the second body and the first opening 44 of the second body are capable of being operatively connected to the second end 24 of the first body and the second opening 28 of the first body. In one instance, the operative connection is capable of providing a substantially gastight connection between the first opening 44 of the second body and the second opening 28 of the first body.

The first end 62 of the third body and the first opening 64 of the third body are capable of being operatively connected to the second end 48 of the second body and the second opening 46 of the second body. In one instance, that operative connection is capable of providing a substantially gastight connection between the first opening 64 of the third body and the second opening 46 of the second body.

The operative connections between the first body 20 and the second body 40 and between the second body 40 and the third body 60 permit fluid flow through the respective passageways 32, 52, 72 thereof. The bodies are also referred to as being in fluid connection.

At least a portion of a surface 54 of the second body 40 is at least partially transparent to electromagnetic radiation in a given range of wavelengths. At least a portion of the passageway 52 of the second body forms a measurement region with a predetermined optical pathlength.

In a further embodiment, a portion of the third body 60 is adapted to enable acquisition of a sample. In a still further embodiment, the second end 66 of third body 60 is adapted for sample acquisition. In an embodiment, the second end 66 of third body 60 is a sample intake portion.

In an embodiment, the third body 60 is constructed using injection-molded materials in order to provide a very narrow inlet which can be used to minimize sample volume. In another instance, the third body 60 is shaped such that it allows access to a sample container (for example, but not limited to, an Eppendorf® tube, a multi-well plate, etc.). In one aspect, the second end 66 of the third body is flat for contacting a liquid sample. In another aspect, the end is tapered or curved. In still another aspect, the end comprises a slit.

In one embodiment, the material used for the third body 60 is selected such that it has the appropriate hydrophobicity for the intended application. In one instance, a hydrophobic material would be appropriate to minimize the quantity of fluid remaining on the lower outside surface of the third body 60. By way of example, the body could be injection-molded, formed or machined from polypropylene, a polyolefin, fluoropolymer and the like. Alternatively, the parts could be coated with a hydrophobic coating. In an embodiment of a hydrophobic coating material includes a siloxane. In another embodiment, the coating includes polydimethyl-siloxane silicon rubber, PTFE (e.g., Teflon®, a polyacrylate, and the like, but this invention is not limited to only these exemplary embodiments.

In an embodiment, the third body 60 is formed from a hydrophobic material in order to minimize binding of liquid sample components. In a further embodiment, where the liquid sample contains protein for evaluation or processing, a hydrophobic material is selected for the third body 60 in order to minimize protein binding. The material of appropriate hydrophobicity can comprise the entire third body 60 or a portion thereof.

In an embodiment, the first end 22 of the first body 20 and the first opening 26 of the first body 20 are capable of operatively connecting to a device for aspirating fluid, e.g., such as a pipette (a "pipette" as used herein, unless otherwise specified, refers to that aspiration causing portion of a pipette e.g., such as a Pipetman®, a Gilsong®, Rainin®, Eppendorf® or Finnipipette® pipette, and may also be referred to as "pipettor") or a rubber bulb, a fluid-delivery device, or to an interface to such a device (e.g., to a pipette tip). In operation, the device for aspirating fluid may be used for aspirating a liquid sample into one or a combination of the respective passageways 32, 52, or 72. In one instance, the material used in the first body 20 is a plastic which may be selected based on material and/or economic considerations.

In another embodiment, the first body 20 is constructed such that it allows a user to handle the apparatus manually. In another embodiment, the first body 20 is adapted for connection to the first body of another apparatus in order to enable the substantially simultaneous selection of multiple samples.

Example 2

In another embodiment, an apparatus for handling a liquid sample is structured similarily to a cuvette. Liquid sample is delivered into an upper portion, wherein it passes downward through a sample processing component, and into a sample evaluation component, for ready evaluation, for example, by UN/VIS spectroscopy. One such embodiment is further described below.

Figure 3:
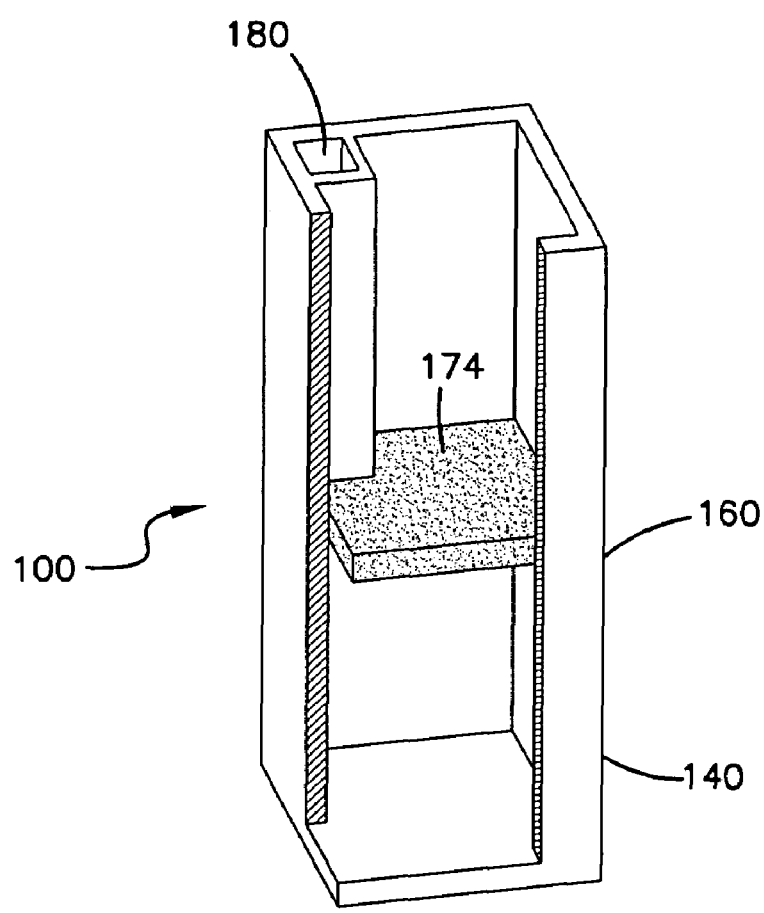
FIG. 3 is a sectional view of another embodiment of an apparatus of the present invention.

Another embodiment of an apparatus is illustrated in FIG. 3. In FIG. 3, apparatus 100 includes two bodies, second body 140 and third body 160, integrated into a single structure. Third body 160 corresponds to roughly the upper portion of apparatus 100. Third body 160 includes solid matrix material 174 positioned horizontally within apparatus 100 and an air vent 180 through solid matrix material 174. Air vent 180 is integrated with the wall of apparatus 100 and extends to the top thereof. In an alternative embodiment, air vent 180 is supplied as a separate structure. Air vent 180 allows liquid sample to be drawn or pushed through the matrix material by gravity, vacuum or applied air pressure. Second body 140 receives liquid sample from third body 160 through solid matrix material 174. In an embodiment, second body 140 Second body 140 is constructed of a semi-transparent or transparent material on at least two opposing sides to allow evaluation of liquid sample collected in the lower portion is constructed of a semi-transparent or transparent material to allow evaluation of liquid sample collected in the lower portion.

Example 3

In yet another embodiment, an apparatus for handling a liquid sample is structured similarity to a centrifuge tube. Liquid sample is delivered into an upper portion into contact with a sample processing component. The sample passes through a sample processing component, for example by gravity or centrifugal force, to a sample evaluation component, for ready evaluation, for example, by UV/VIS spectroscopy. One such embodiment is further described below.

Figure 4:
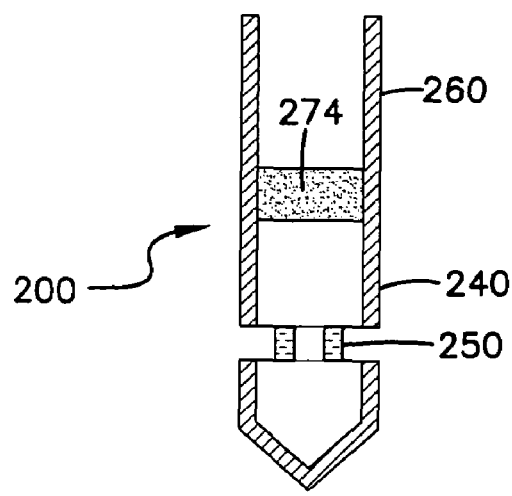
FIG. 4 is a schematic representation with a portion cut-away of yet another embodiment of an apparatus of the present invention.

Yet another embodiment of an apparatus is illustrated in FIG. 4. Apparatus 200, shown in FIG. 4 includes two bodies, second body 240 and third body 260, integrated into a single structure. Third body 260 corresponds to roughly the upper portion of apparatus 200. Third body 260 includes solid matrix material 274 positioned horizontally within apparatus 200. Second body 240 is below third body 260 and solid matrix material 274 and receives liquid sample from third body 260 through solid matrix material 274. Second body 240 includes a portion 250 constructed of a semi-transparent or transparent material to allow evaluation of liquid sample collected in the lower portion. In an embodiment, liquid sample is pushed through solid matrix materials 274 into second body 240 by application of centrifugal force.

Methods

An apparatus for handling a liquid sample, wherein the apparatus includes integrated sample processing and sample evaluating components is used for processing and evaluating of a liquid sample. In an embodiment, an apparatus includes two or more bodies, wherein liquid sample is processed by components for integrated sample processing in one body and wherein liquid sample is evaluated in another body containing sample evaluating components. In a further embodiment, the bodies are modular portions that operably connect. In an alternative embodiment, the bodies are included or constructed in a unified structure.

In an embodiment, a method of using an apparatus including a first body with at least one sample processing component and a second body with at least one sample evaluation component includes applying a liquid sample to the first body for processing of the liquid sample with the at least one sample processing component therein, and evaluating the constituents for evaluation in the liquid sample with the at least one sample evaluation component of the second body. In a further embodiment, the method includes additional processing of the liquid sample by additional sample processing components. In a still further embodiment, additional processing of the liquid sample occurs downstream from the second body.

In an embodiment, the method includes flowing the liquid sample through the first body and a sample processing component. In an embodiment, the method includes at least partially removing one or more contaminates from the liquid sample. In a further embodiment, a sample processing component includes resin, membrane, frit or other solid matrix material with adsorbent properties, such that the contaminants bind to the resin, membrane, frit, solid matrix material, as the liquid sample moves through the first body. In an embodiment, the method includes at least partially separating particulate, whole cells and cell fragments from the liquid sample.

In an embodiment, the method includes flowing the liquid sample through the first body and contacting a sample processing component. In a further embodiment, the method includes adding a least one sample processing component to the liquid sample. In an embodiment, the method includes reacting the liquid sample reacts with an added component.

In an embodiment, the method includes applying a liquid sample to the first body and subsequently evaluating the sample by the second body. In a further embodiment, the method includes performing further sample processing after evaluation of the sample by the second body.

In an embodiment, the method includes collecting a quantity of liquid sample in the evaluation component of the second body portion of the apparatus after flowing through the first body. In a further embodiment, the method includes collecting a quantity of liquid sample in a portion of the apparatus, the portion being in addition to the evaluation component or in alternative to the evaluation component.

In an embodiment, the method includes evaluating a volume of liquid sample evaluated with the evaluation component is less than 500 microliters. In an embodiment, the method includes evaluating a volume of liquid sample evaluated with the evaluation component is less than 100 microliters. In an embodiment, the method includes evaluating a volume of liquid sample evaluated with the evaluation component is less than 10 microliters. In an embodiment, the method includes evaluating a volume of liquid sample evaluated with the evaluation component is less than 1 microliter.

In an embodiment, evaluating the liquid sample includes performing UV/VIS spectroscopy. In an embodiment, evaluating the liquid sample includes measuring of absorbed spectra of the sample. The light absorbance of a sample depends on the pathlength L of light passing through the sample, as well as on the concentration of light absorbers (e.g., biomolecules, cells, etc) in a sample solution and the wavelength ($\lambda$) of light being used to characterize the sample. The wavelengths of UV-Visible light span from 200 nm to 800 nm, while ultraviolet wavelengths range from 200 to 400 nm. In an embodiment, the sample evaluation component comprises windows sufficiently transparent to allow optical measurement in a range of about 200-1100 nm. In an embodiment, the sample evaluation component comprises windows sufficiently transparent to allow optical measurement in a range of about 300-800 nm.

UV-Visible spectrophotometry provides a convenient analysis technique to determine the concentration, purity, and integrity of a biological sample without requiring additional sample preparation other than acquiring a sample. UV-Visible Spectrophotometry measurements depend on the light source (UV lamp), the sample and sampling technique. Most biological samples absorb electromagnetic radiation at wavelengths ranging from 200 nm to 800 nm, mostly 230, 260 and 280 nm. For a DNA or RNA sample in aqueous phase, one unit of absorbance measured at a wavelength of 260 nm and a pathlength of 10 mm is equal to 50/(40) ng/ml concentration.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention without following the example embodiments and applications illustrated and described herein, and without departing from the true spirit and scope of the present invention, which is set forth in the following claims.

The claimed invention is:

1. An apparatus for handling a liquid sample, the apparatus comprising:
   an intake body operatively connected to a measurement body, wherein the intake body comprises a sample intake portion, an internal passageway, a sample processing component located within the passageway, the sample processing component comprising a solid matrix that separates at least one component from the sample; and
   the measurement body comprising an internal passageway and a sample evaluation component with an optical pathlength, wherein the sample evaluation component comprises a window at least partially transparent to electromagnetic radiation; and
   wherein the intake body is connected to the measurement body such that the sample flows from the intake body to the measurement body through the sample processing component, and wherein the first and measurement body have a different optical property.

2. The apparatus of claim 1, wherein the internal passageway of the measurement body in the sample evaluation component is dimensioned to hold liquid sample by capillary action.

3. The apparatus of claim 1, further comprising an aspiration body connected to the measurement body, the aspiration body being configured for operatively connecting to a device for aspirating liquid.

4. The apparatus of claim 1, further comprising one or more additional integrated sample processing components.

5. The apparatus of claim 1, wherein at least one additional integrated sample processing component is located upstream from the sample evaluation component.

6. The apparatus of claim 1, wherein the sample processing component comprises an affinity molecule or chemical reactant.

7. The apparatus of claim 1, wherein the window comprises a material selected from the group consisting of polyimide, polycarbonate, polystyrene, polyolefin, fluoropolymer, polyester, polyvinylidene chloride, polyhalocarbon, glass, quartz, silica, crosslinked dimethyldisiloxane, sapphire or garnet.

8. The apparatus of claim 1 wherein the sample evaluation component comprises a window sufficiently transparent to allow optical measurement in a range of about 200-1100 nm.

9. The apparatus of claim 1 wherein the sample evaluation component comprises a window sufficiently transparent to allow optical measurement in a range of about 300-800 nm.

10. A method of using an apparatus comprising an intake body with at least one sample processing component and a measurement body with at least one sample evaluation component, the intake and measurement bodies operatively connected, the method comprising:

applying a liquid sample comprising constituents for evaluation and contaminates to the intake body;

removing at least some contaminates from the liquid sample by flowing the liquid sample through at least one sample processing component comprising a solid matrix that separates one or more contaminants of the sample into the measurement body and wherein the intake and measurement body have different optical properties; and evaluating the constituents for evaluation in the liquid sample with at least one sample evaluation component of the measurement body.

11. The method of claim 10, wherein the contaminants comprise particulate, whole cells, and cell fragments.

12. The method of claim 10, wherein the sample processing component comprises resin, membrane, frit or solid matrix material with adsorbent properties, such that the contaminants couple to the resin, membrane, frit, solid matrix material, or components thereof for removal from the liquid sample.

13. The method of claim 10, wherein the sample processing component comprises one or more affinity molecules or chemical reactants to the liquid sample.

14. The method of claim 10, wherein the volume of liquid sample evaluated with the sample evaluation component is less than 100 microliters.

15. The method of claim 10, wherein the volume of liquid sample evaluated with the sample evaluation component is less than 10 microliters.

* * * * *